(12) United States Patent
Newman et al.

(10) Patent No.: US 7,557,918 B1
(45) Date of Patent: Jul. 7, 2009

(54) SPECTRAL POLARIMETRIC IMAGE DETECTION AND ANALYSIS METHODS AND APPARATUS

(75) Inventors: J. Daniel Newman, Pittsford, NY (US);
Paul P. Lee, Pittsford, NY (US); Eric J. Knappenberger, Webster, NY (US);
Rulon Simmons, Rochester, NY (US);
Andre Dominic Cropper, Rochester, NY (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 295 days.

(21) Appl. No.: 11/397,976

(22) Filed: Apr. 5, 2006

(51) Int. Cl.
*G01J 4/00* (2006.01)

(52) U.S. Cl. ................................... 356/369

(58) Field of Classification Search ............. 356/367, 356/369
See application file for complete search history.

(56) References Cited

U.S. PATENT DOCUMENTS

| | | |
|---|---|---|
| 4,776,692 A | 10/1988 | Kalawsky |
| 4,912,059 A | 3/1990 | Newman et al. |
| 5,005,977 A | 4/1991 | Tomoff |
| 5,011,295 A | 4/1991 | Krishnan et al. |
| 5,046,850 A | 9/1991 | Tomoff |
| 5,131,742 A | 7/1992 | Schaff |
| 5,247,176 A | 9/1993 | Goldstein |
| 5,296,913 A | 3/1994 | Heffner |
| 5,317,150 A | 5/1994 | Norris et al. |
| 5,440,390 A | 8/1995 | Tirri |
| 5,519,493 A | 5/1996 | Reiley |
| 5,666,201 A | 9/1997 | Johs et al. |
| 5,706,212 A | 1/1998 | Thompson et al. |
| 5,737,298 A | 4/1998 | Suhan |
| 5,956,145 A | 9/1999 | Green et al. |
| 5,963,327 A | 10/1999 | He et al. |
| 6,046,805 A | 4/2000 | Kawamura et al. |
| 6,166,807 A | 12/2000 | Kawamura et al. |
| 6,175,412 B1 | 1/2001 | Drevillon et al. |
| 6,177,995 B1 | 1/2001 | Compain et al. |
| 6,181,421 B1 | 1/2001 | Aspnes et al. |
| 6,211,957 B1 | 4/2001 | Erdogan et al. |
| 6,268,916 B1 | 7/2001 | Lee et al. |
| 6,327,037 B1 | 12/2001 | Chou et al. |
| 6,370,407 B1 | 4/2002 | Kroeger et al. |
| 6,466,320 B1 | 10/2002 | Kawamura et al. |
| 6,535,286 B1 | 3/2003 | Green et al. |
| 6,549,282 B1 | 4/2003 | Johs et al. |
| 6,583,410 B1 | 6/2003 | Seddon |
| 6,608,587 B1 | 8/2003 | Sparrow et al. |
| 6,640,116 B2 | 10/2003 | Diab |
| 6,704,106 B2 | 3/2004 | Anderson et al. |
| 6,713,753 B1 | 3/2004 | Rovira et al. |
| 6,717,665 B2 | 4/2004 | Wagner et al. |
| 6,734,968 B1 | 5/2004 | Wang et al. |
| 6,744,509 B2 | 6/2004 | Davis et al. |
| 6,762,713 B1 | 7/2004 | McMillan et al. |
| 6,765,672 B1 | 7/2004 | Veasey |

(Continued)

*Primary Examiner*—Roy Punnoose
(74) *Attorney, Agent, or Firm*—RatnerPrestia

(57) ABSTRACT

Apparatus and methods for detecting and analyzing spectral polarimetric images are disclosed. Spectral polarimetric images are detected by selecting spectral bands of light within light received from a light source and capturing polarimetric images of the selected spectral bands of light. Spectral polarimetric images are analyzed by converting spectral polarimetric images to Stokes images and selecting two or more of the Stokes images for analysis.

20 Claims, 8 Drawing Sheets

U.S. PATENT DOCUMENTS

| | | |
|---|---|---|
| 6,768,971 B1 | 7/2004 | Sparrow et al. |
| 6,795,184 B1 | 9/2004 | Herzinger et al. |
| 6,798,514 B2 | 9/2004 | Daniels |
| 6,801,320 B2 | 10/2004 | Szafraniec |
| 6,804,003 B1 | 10/2004 | Wang et al. |
| 6,804,004 B1 | 10/2004 | Johs et al. |
| 6,816,260 B2 | 11/2004 | Peupelmann et al. |
| 6,836,327 B1 | 12/2004 | Yao |
| 6,856,398 B2 | 2/2005 | Ruchet |
| 6,867,853 B2 | 3/2005 | Ro et al. |
| 6,885,333 B2 | 4/2005 | Sparrow et al. |
| 6,917,427 B2 | 7/2005 | Krause et al. |
| 6,927,888 B2 | 8/2005 | Garcia et al. |
| 6,950,611 B2 | 9/2005 | Erdogan et al. |
| 7,420,675 B2 * | 9/2008 | Giakos ......... 356/364 |
| 2002/0186468 A1 | 12/2002 | Lee et al. |
| 2003/0117624 A1 | 6/2003 | Daniels |
| 2003/0174328 A1 | 9/2003 | Russell et al. |
| 2003/0223064 A1 | 12/2003 | Anderson et al. |
| 2004/0012853 A1 | 1/2004 | Garcia et al. |
| 2004/0036876 A1 | 2/2004 | Davis et al. |
| 2004/0064064 A1 | 4/2004 | Zhou et al. |
| 2004/0070766 A1 | 4/2004 | Szafraniec |
| 2004/0145728 A1 | 7/2004 | Kim et al. |
| 2005/0062966 A1 | 3/2005 | Chen et al. |
| 2005/0105088 A1 | 5/2005 | Garcia-Caurel et al. |
| 2005/0264813 A1 * | 12/2005 | Giakos ......... 356/369 |

* cited by examiner

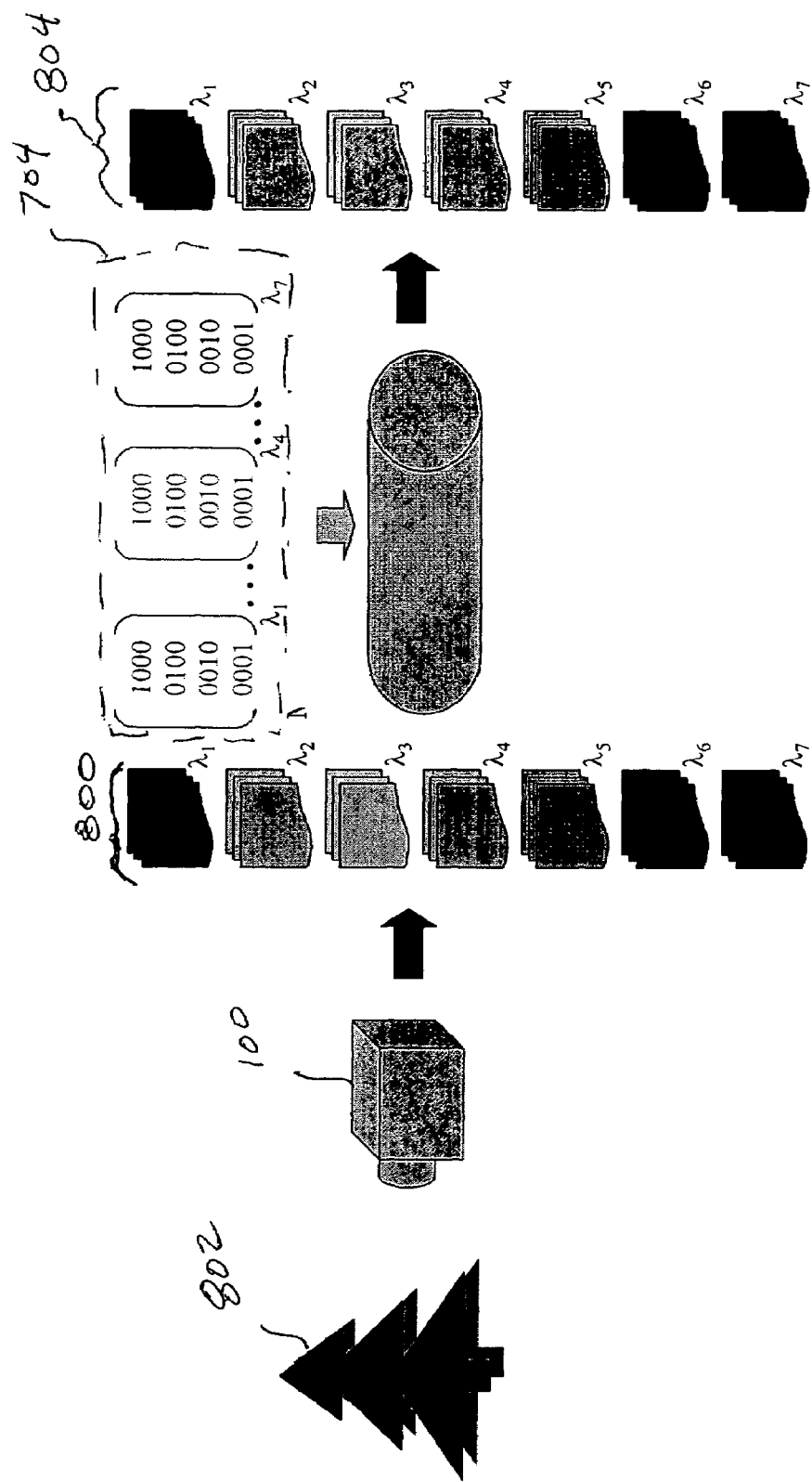

SPECTRAL POLARIMETRIC IMAGE DETECTION AND ANALYSIS METHODS AND APPARATUS

CROSS REFERENCE TO RELATED APPLICATIONS

Reference is made to commonly assigned copending application Ser. No. 11/021,258 entitled "Programmable Spectral Imaging System" by Marek W. Kowarz, James G. Phalen, and J. Daniel Newman, filed Dec. 21, 2004 and Ser. No. 11/316,857 entitled "Imaging System with a Programmable Spectral Switch" by Marek W. Kowarz, James G. Phalen, and J. Daniel Newman, filed Dec. 23, 2005, which are both incorporated fully herein by reference.

FIELD OF THE INVENTION

The present invention relates to imaging systems and, more particularly, to methods and apparatus for detecting and analyzing spectral polarimetric images.

BACKGROUND OF THE INVENTION

Imaging systems are used to collect images. The collected images are often analyzed, e.g., to identify objects of interest within the images. Spectral imaging systems or polarimetric imaging systems may be employed to collect images in one or more spectral bands or in one or more polarimetric states (e.g., 0°, 45°, 90°, and 135°), respectively, to facilitate the identification of some objects during analysis.

Spectral imaging systems and polarimetric imaging systems are typically separate physical instruments that collect distinct images. In order to interpret an image collected by both a spectral imaging system and a polarimetric imaging system, images obtained by each of these systems need to be co-registered. Co-registering images from separate imaging systems, however, is difficult. This problem is further exacerbated by the ever increasing resolution of imaging systems.

SUMMARY OF THE INVENTION

The present invention is embodied in apparatus and methods for detecting and analyzing spectral polarimetric images. Spectral polarimetric images are detected in accordance with one aspect of the present invention by selecting spectral bands of light within light received from a light source and capturing polarimetric images of the selected spectral bands of light. Spectral polarimetric images are analyzed by converting spectral polarimetric images to Stokes images and selecting two or more of the Stokes images for analysis.

An apparatus for detecting light received from a light source in accordance with one aspect of the present invention includes a tunable spectral selector and a polarimetric imager optically coupled to the tunable spectral selector. The tunable spectral selector selects one or more spectral bands of light within the received light and the polarimetric imager receives and captures the selected one or more spectral bands of light.

Spectral polarimetric images representing the intensity of an image in each of two or more polarization states in each of two or more wavelength bands are analyzed in accordance with one aspect of the present invention by converting the spectral polarimetric images for each of the two or more polarization states in each of the two or more wavelength bands to Stokes images and selecting two or more Stokes images for analysis.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale. On the contrary, the dimensions of the various features are arbitrarily expanded or reduced for clarity. Included in the drawings are the following figures:

FIG. 8 is a conceptual illustration of a procedure for generating Stokes images from spectral polarimetric images in accordance with aspects of the present invention.

DETAILED DESCRIPTION OF THE INVENTION

Figure 1:
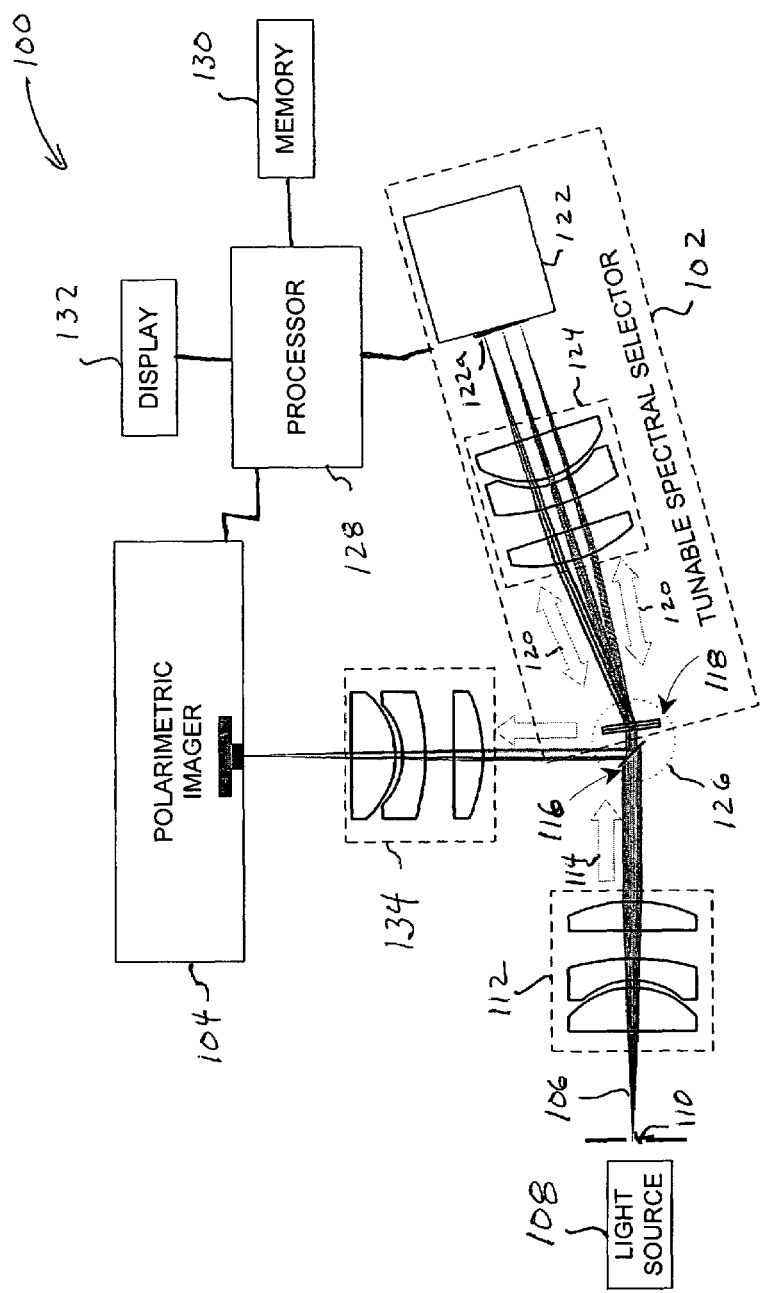
FIG. 1 is a block diagram of an exemplary spectral polarimetric detector in accordance with aspects of the present invention.

FIG. 1 depicts an exemplary spectral polarimetric detector 100 in accordance with an aspect of the present invention. The illustrated detector 100 includes tunable spectral selector 102 that is optically coupled to polarimetric imager 104, each of which are described in detail below. Polarimetric imager 104 detects polarimetric images of light 106 received from light source 108 over one or more spectral wavelength bands as selected by tunable spectral selector 102. Thus, spectral polarimetric detector 100 is capable of simultaneously detecting spectral band information and polarimetric information associated with an image for interpretation without the need to co-register spectral and polarimetric images obtained from separate imaging devices as in the prior art. As used herein, the term "spectral polarimetric image" refers to an image having one or more selected wavelengths and one or more selected polarimetric states, e.g., an image having wavelength of 600-620 nm and a 45° polarimetric state.

In an exemplary embodiment, light 106 carries an image that is received by detector 100 through input slit 110. Light 106 received by detector 100 is directed to tunable spectral selector 102 where one or more spectral bands of light 106 are selected for detection. In an exemplary embodiment, input lens assembly 112 directs light 106 along optical path 114 through light path selector 116 (described in further detail below) positioned along optical path 114 toward tunable spectral selector 102.

Tunable spectral selector 102 illustrated in FIG. 1 includes grating 118 that disperses light 106 to obtain dispersed light 120 and further includes spectral selection device 122 that selects one or more spectral bands of light from within dispersed light 120. Grating 118 and spectral selection device 122 are positioned relative to one another such that at least a portion of dispersed light 120 impinges on imaging surface 122a of spectral selection device 122. Dispersed light lens assembly 124 that includes one or more lenses (represented by three lens in the illustrated embodiment) may be employed to direct the dispersed light between grating 118 and spectral selection device 122 and to focus the dispersed light onto imaging surface 122a of spectral selection device 122. Other suitable tunable spectral selectors 102 will be understood by one of skill in the art from the description herein. In addition, alternative exemplary tunable spectral selectors 108 are described in commonly assigned copending application Ser. No. 11/021,258 entitled "Imaging System with a Programmable Spectral Switch" by Marek W. Kowarz, James G. Phalen, and J. Daniel Newman, filed Dec. 23, 2005, which is incorporated fully herein by reference.

In an exemplary embodiment, grating 118 is a transmission grating that disperses light 106 as it passes through the grating 118. In an alternative exemplary embodiment, grating 118 may be a reflection grating that disperses light 106 as it is reflected by grating 118.

In an exemplary embodiment, spectral selection device 122 is a reflective device that selectively diffracts/reflects light incident on imaging surface 122a to select the one or more spectral bands. In accordance with this embodiment, imaging surface 122a may include a plurality of addressable segments that selectively diffract/reflect dispersed light 120 responsive to a spectral selection signal (e.g., generated by processor 128, which is described below). In an exemplary embodiment, grating 118 and spectral selection device 122 are selected and positioned relative to one another such that grating 118 essentially "smears" the light 106 from input slit 110 across imaging surface 122a of spectral selection device 122. Thus, the wavelengths of light 106 are spread across imaging surface 122a for selection thereof.

An exemplary reflective device for use as spectral selection device 122 is an electromechanical conformal grating device consisting of ribbon elements suspended above a substrate by a periodic sequence of intermediate supports. The electromechanical conformal grating device is operated by electrostatic actuation, which causes the ribbon elements to conform around the support substructure, thereby producing a grating. This device is commonly referred to as the conformal GEMS device, or more simply as the GEMS device, with GEMS standing for Grating Electro-Mechanical System. The GEMS device provides high-speed digital light modulation with high contrast, high efficiency, and a relatively large addressable active region. The GEMS device can be fabricated as a linear device with a thin active area in order to diffract a thin line of the dispersed light (e.g., to select narrow wavelength bands) or can be fabricated with a relatively wide active area in order to diffract a wider segment of the dispersed light (e.g., to select wide wavelength bands).

The behavior of GEMS devices and systems is described in commonly assigned U.S. Pat. No. 6,307,663; in commonly assigned U.S. Pat. No. 6,411,425 entitled "Electromechanical Grating Display System With Spatially Separated Light Beams"; and in commonly assigned U.S. Pat. No. 6,678,085 entitled "High-Contrast Display System With Scanned Conformal Grating Device" all to Kowarz et al., all of which are incorporated by reference herein.

Figure 2:
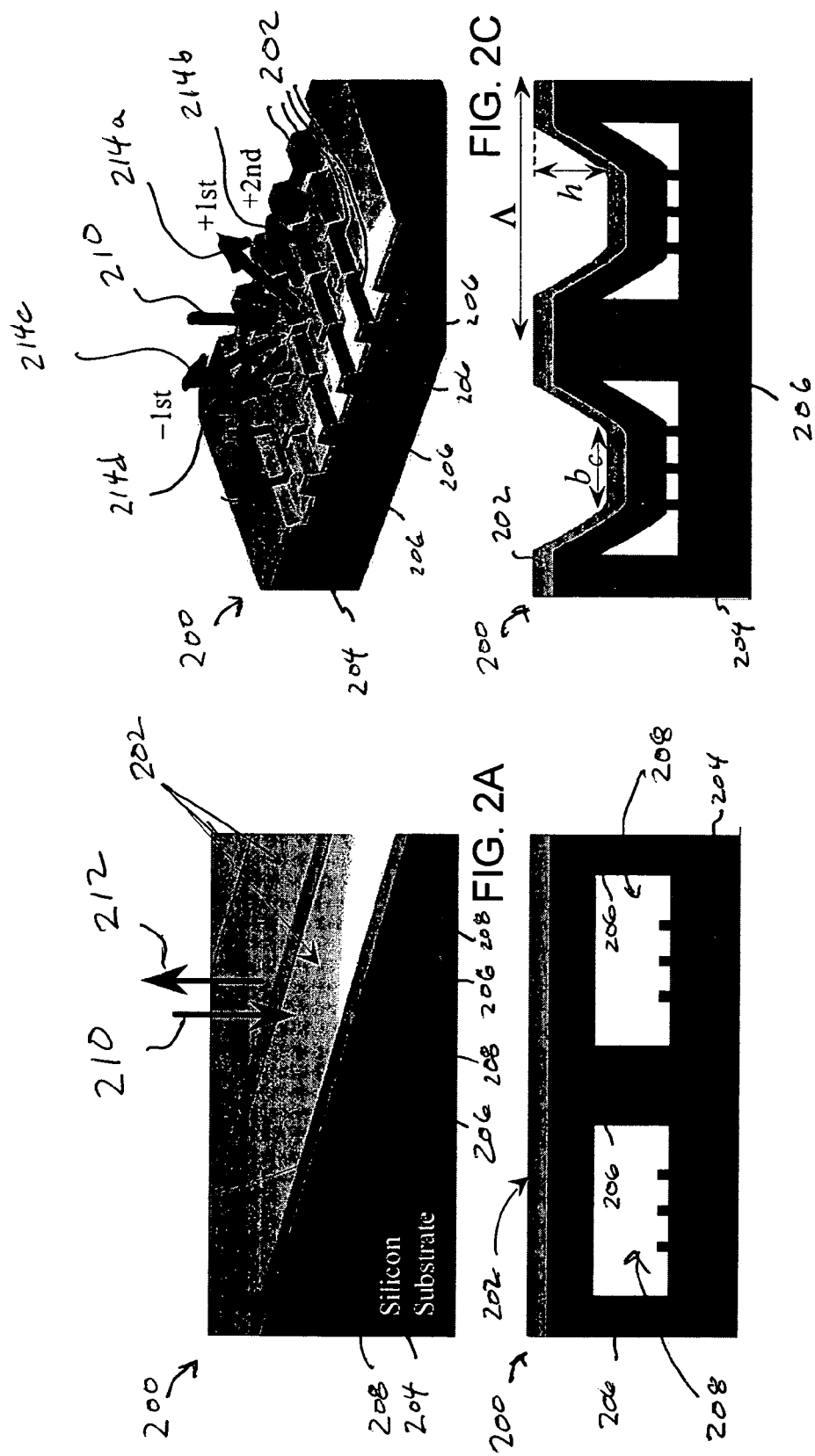
FIGS. 2A, 2B, 2C, and 2D are conceptual illustrations of a Grating Electro-Mechanical System (GEMS) device for use as a spectral selection device in the exemplary spectral polarimetric detector of FIG. 1 in accordance with aspects of the present invention.

FIGS. 2A-2D are conceptual illustrations of GEMS device 200 for use as spectral selection device 122. FIGS. 2A and 2B depict a perspective view and a side view, respectively, of GEMS device 200 in an off state (i.e., reflective state) and FIGS. 2C and 2D depict a perspective view and a side view, respectively, of GEMS device 200 in an on state (i.e., diffractive state). GEMS device 200 includes a plurality of ribbons 202 that are suspended over a substrate 204 such as Silicon by intermediate supports 206, thereby forming a plurality of cavities 208 under the ribbons 202. In an exemplary embodiment, the distance between intermediate supports 206 is approximately 10 to 60 μm and ribbons 202 are drawn into the cavities approximately 100 to 200 nm when in the on state.

In an exemplary embodiment, each of cavities 208 (or a row of cavities) are individually addressable. When an addressable cavity 208 is off, the ribbon 202 above the cavity reflects incident beam 210 of light back along the path of incident beam 210 as reflected light 212 such as illustrated in FIG. 2A. When an addressable cavity 208 is on, the portion of ribbon 202 above that cavity is drawn into cavity 208, thereby causing incident beam 210 to diffract as diffracted light 214a-d such as illustrated in FIG. 2C. FIG. 2C illustrates the positive first and second order diffractions 214a, b and the negative first and second order diffraction 214c, d for an incident beam 210 being diffracted by the GEMS device 200. Thus, GEMS device 200 may be used to select one or more spectral band by activating the cavities 208 under the imaging surface associated with those spectral bands.

Alternative exemplary spectral selection devices 116 include a Digital Micromirror Device (DMD) used in Digital Light Processor (DLP) systems manufactured by Texas Instruments, Inc., Dallas, Tex. and known Liquid Crystal on Silicon (LCOS) light modulators. Other suitable spectral selection devices will be understood by one of skill in the art from the description herein and are considered within the scope of the present invention.

Referring back to FIG. 1, in the illustrated embodiment, the dispersed light as diffracted/reflected by spectral selections device 122 is passed back to grating 118, which collimates the light. The collimated diffracted/reflected light then passes back to light path selector 116. In an exemplary embodiment, light path selector 116 directs the light diffracted by spectral selection device 122 toward polarimetric imager 104 and directs the light reflected by spectral selection device 122 away from polarimetric imager 104. In an exemplary embodiment, light path selector 116 and transmission grating 118 are positioned within a Fourier transform plane 126 of input lens assembly 112.

Figure 3:
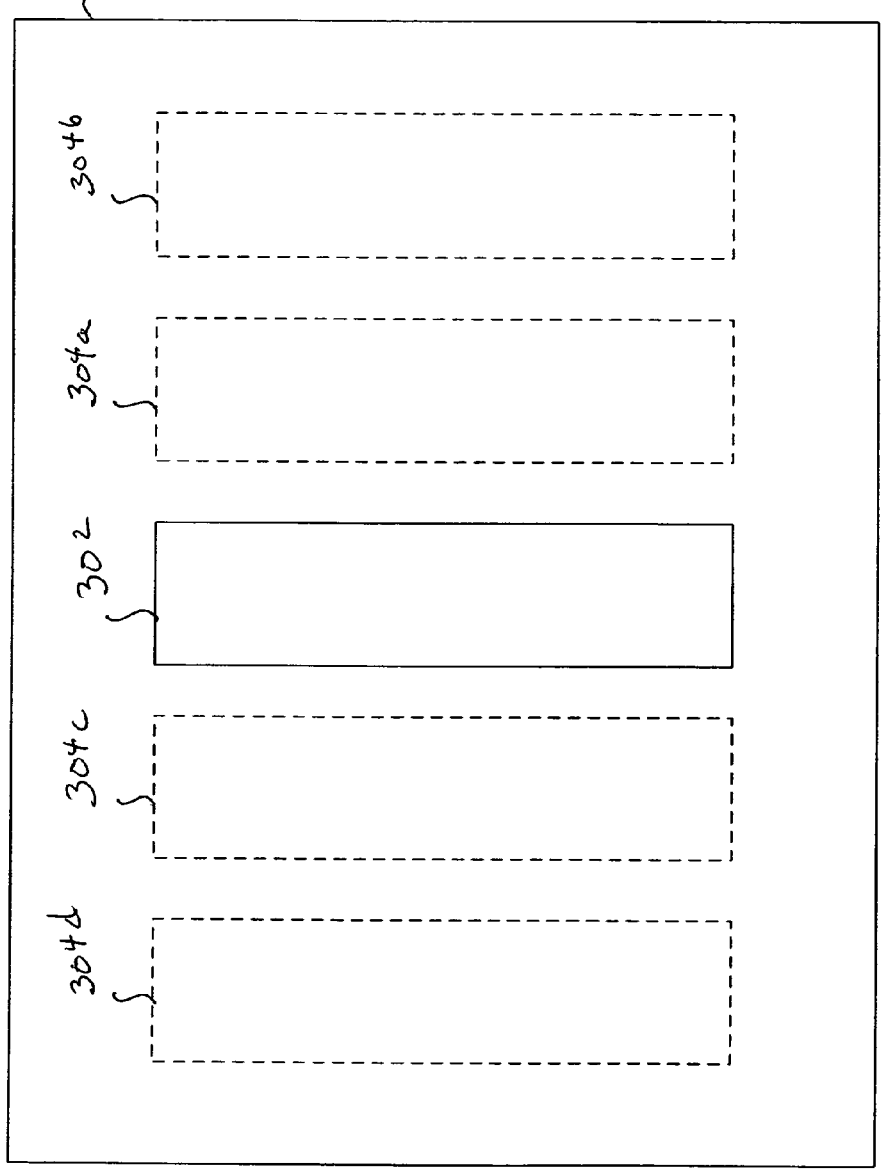
FIG. 3 is a conceptual illustration of a patterned mirror for use as a light path director in the exemplary spectral polarimetric detector of FIG. 1 in accordance with aspects of the present invention.

FIG. 3 depicts an exemplary light path selector 116. The illustrated light path selector 116 is a patterned mirror 300. Patterned mirror 300 includes slot 302 through which light may pass and one or more reflective regions that reflect light (represented by four reflective regions 304a-d in the illustrated embodiment). In an exemplary embodiment, slot 302 allows light reflected by spectral selection device 122 to pass, thereby directing the light away from polarimetric imager 104. In addition, first reflective region 304a reflects positive first order diffraction 214a (FIG. 2C) from spectral selection device 122, second reflective region 304b reflects positive second order diffraction 214b (FIG. 2C) from spectral selection device 122, third reflective region 304c reflects negative first order diffraction 214c (FIG. 2C) from spectral selection device 122, and fourth reflective region 304d reflects negative second order diffraction 214d (FIG. 2D) from spectral selection device 122, thereby directing the light toward polarimetric imager 104. Patterned mirror 300 may be sized and shaped to reflect different diffractive orders and different shapes, e.g., square, rectangular, circular, oval, or other geometric shape. In alternative exemplary embodiments, light path selector 116 (FIG. 1) may be a dichroic element.

Referring back to FIG. 1, polarimetric imager 104 captures polarimetric images of the light as spectrally selected by tunable spectral selector 102, thereby capturing spectral polarimetric images. In an exemplary embodiment, polarimetric imager 104 captures polarimetric images in four different polarimetric states (e.g., polarimetric angles 0°, 45°, 90°, and 135°). The light may be directed to polarimetric imager 104 and focused thereon by spectrally selected lens assembly 134 of one or more lens (represented by three lenses in the illustrated embodiment).

Figure 4:
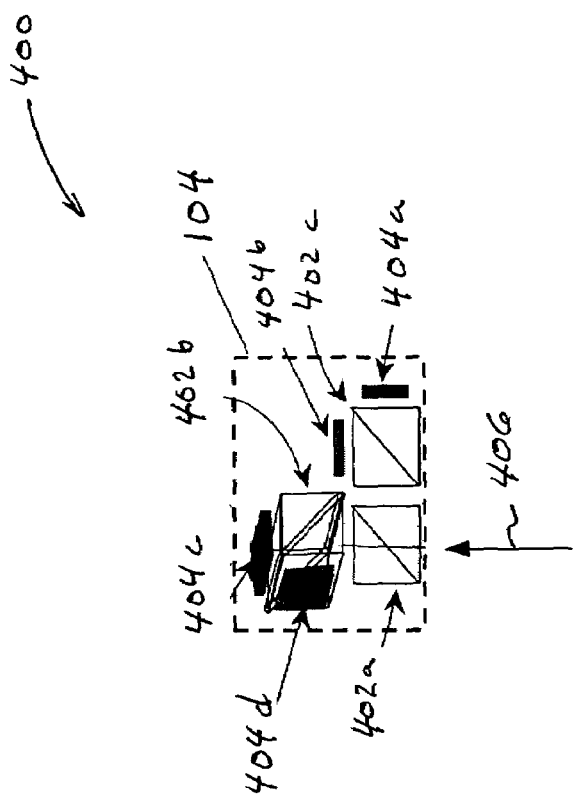
FIG. 4 is a conceptual illustration of a polarimetric imager for use in the exemplary spectral polarimetric detector of FIG. 1 in accordance with aspects of the present invention.

FIG. 4 is a conceptual illustration of a polarimetric imager 400. The illustrated polarimetric image 400 includes three beam splitters 402a-c and four sensors 404a-d. Light received from tunable spectral selector 102 along light path 406 impinges on a surface of first beam splitter 402a. First beam splitter 402a allows a portion of the light to pass toward second beam splitter 402b and redirects a portion of the light toward third beam splitter 402c. Third beam splitter 402c, which received the light redirected by first beam splitter 402a, allows a portion of that light to pass to first sensor 404a and redirects a portion of that light to second sensor 404b. Second beam splitter 402b, which received light passed by first beam splitter 402a, passes a portion of that light to third sensor 404c and redirects a portion of that light to fourth sensor 404d. Suitable sensors and beam splitters for use in with the present invention will be understood by one of skill in the art from the description herein.

In an exemplary embodiment, first beam splitter 402a is a 50/50 beam splitter that splits the incident light substantially equally, second beam splitter 402b is a 45°/135° polarimetric beam splitter, and third beam splitter 402c is a 0°/90° polarimetric beam splitter. The beam splitters and sensors are arranged such that first sensor 404a captures the 0° polarimetric angle of the spectrally selected light, second sensor 404b captures the 90° polarimetric angle of the spectrally selected light, third sensor 404c captures the 45° polarimetric angle of the spectrally selected light, and fourth sensor captures the 135° polarimetric angle of the spectrally selected light. Although the 0°, 45°, 90°, and 135° polarimetric angles are captured, as will be recognized by one of skill in the art from the description herein, essentially any angles and number of angles of light may be sensed by repositioning the beam splitters and sensors and/or using different beam splitters.

In an alternative exemplary embodiment, the polarimetric imager 104 (FIG. 1) includes a single sensor and one or more polarization filters, such as one or more filters implementing a mosaic approach (also known as a Bayer pattern), that spatially encodes polarimetric images onto the single sensor. For example, a polarization filter may be employed that passes light in each of four polarimetric states to particular pixels on the sensor corresponding to those polarimetric states. Exemplary Bayer pattern techniques are described in U.S. Pat. No. 3,971,065 to Bayer entitled "Color Imaging Array," which is incorporated fully herein by reference. Other suitable polarimetric imagers for use with the present invention will be understood by one of skill in the art from the description herein and are considered within the scope of the present invention.

Referring back to FIG. 1, processor 128 is coupled to tunable spectral selector 102 and polarimetric imager 104. Processor 128 controls tunable spectral selector 102 such that one or more spectral bands of interest are selected. In addition, processor 128 may be used to obtain data from polarimetric imager 104. In an exemplary embodiment, processor 128 is configured to generate the spectral selection signal that controls spectral selection device 122 of tunable spectral selector 102 for selectively diffracting/reflecting dispersed light 112. Processor 128 may store the images in memory 130 and/or may present the images via display 132.

Figure 5:
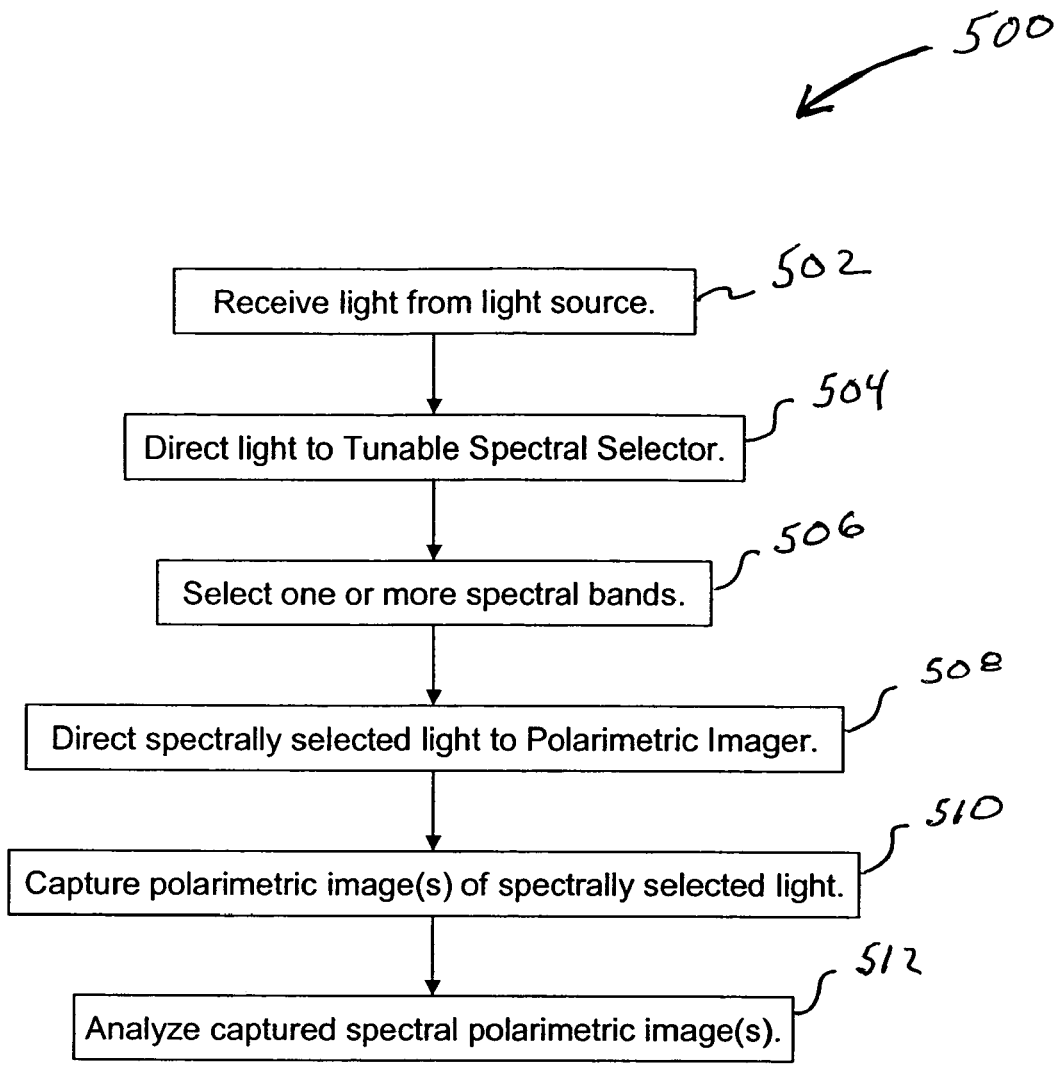
FIG. 5 is a flow chart of exemplary steps for detecting spectral polarimetric images in accordance with aspects of the present invention.

FIG. 5 depicts a flow chart 500 of exemplary steps for detecting light received from a light source. The steps of flow chart 500 are described below with reference to FIG. 1. At block 502, light 106 is received from light source 108 and, at block 504, light 106 is directed to tunable spectral selector 102. In an exemplary embodiment, the light is received through input slit 110 and is directed to tunable spectral selector 102 via input lens assembly 112 and light path selector 116.

At block 506, one or more spectral bands of light within the received light is selected responsive to a spectral selection signal. In an exemplary embodiment, processor 128 generates the spectral selection signal and spectral selection device 122 selects the one or more spectral bands of light responsive to the spectral selection signal. The spectral selection may involve dispersing the received light, selectively diffracting the dispersed light to select the one or more bands of light, and collimating the selectively diffracted one or more bands of light for capturing of the at least one polarimetric image. Grating 118 may disperse the bands of light for selection by spectral selection device 122. In addition, the grating 118 may collimate the light as diffracted/reflected by spectral selection device 122.

At block 508, the spectrally selected light is directed to polarimetric imager 104. In an exemplary embodiment, light path selector 116 directs the spectrally selected light to polarimetric imager 104, e.g., via spectrally selected lens assembly 134, which focuses the spectrally selected light onto a surface of polarimetric imager 104. In an exemplary embodiment, light path selector 116 passes light received through input slit 110 to spectral selection device 122, passes light reflected by spectral selection device 122 away from polarimetric imager 104, and reflects light diffracted by spectral selection device 116 toward polarimetric imager 104 to direct the spectrally selected light to polarimetric imager 104.

At block 510, polarimetric imager 104 captures at least one polarimetric image of the selected one or more spectral bands of light. Thus, spectral polarimetric detector 100 detects spectral polarimetric images. In an exemplary embodiment, polarimetric imager 104 at least substantially simultaneously captures polarimetric images having two or more polarimetric states (e.g., four polarimetric angles such as 0°, 45°, 90°, and 135°).

At block 512, the spectral polarimetric images are analyzed. The spectral polarimetric images may be analyzed by processor 128, e.g., by comparison to other stored images of known objects of interest, or may presented on display 132 for analysis by a human operator.

Figure 6:
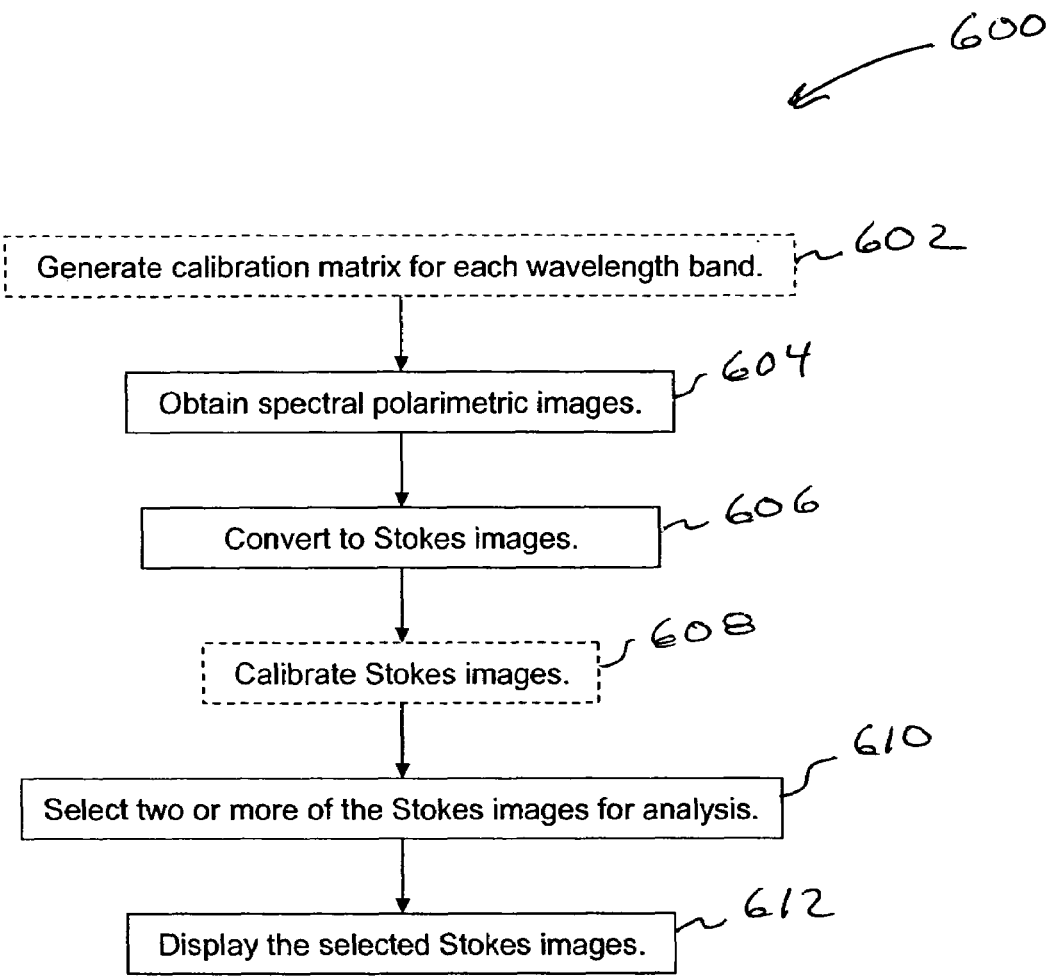
FIG. 6 is a flow chart of exemplary steps for analyzing spectral polarimetric images in accordance with aspects of the present invention.

FIG. 6 depicts a flow chart 600 of exemplary steps for analyzing spectral polarimetric images in accordance with one aspect of the present invention. The spectral polarimetric images represent the intensity of an image in each of two or more polarization states (e.g., a polarization angle of 0°, 45°, 90°, and 135°) in each of two or more wavelength bands.

At block 602, a calibration matrix is generated for each of the two or more wavelength bands. In an exemplary embodiment, each calibration matrix is a Mueller matrix generated using spectral polarimetric image data obtained from polarized calibration images using the spectral polarimetric detector 100 of FIG. 1.

As will be understood by one of skill in the art from the description is herein, an output Stokes vector (e.g., $[S_0\text{-}S_3]_{out}$) is related to an input Stokes vector (e.g., $[S_0\text{-}S_3]_{in}$) through a Mueller matrix (e.g., $[M_{11}\text{-}M_{44}]$) as illustrated in equation 1 below. Thus, the value of the Mueller matrix may be determined by measuring the output Stokes vector when the Stokes vector of the incoming image is known. The number of measurements depends on the number of Stokes vectors. For example, 16 Stokes measurements are used for a set of four Stokes vectors $S_0 \ldots S_3$ and nine Stokes measurements are used for a set of three Stokes vectors. Depending on the configuration of the polarimetric filters, the measurements can be made sequentially or in a parallel fashion. Specifically, for a spectral polarimetric detector capable of capturing all four vectors simultaneously, four separate measurements may be made in a parallel fashion.

$$\begin{bmatrix} S_0 \\ S_1 \\ S_2 \\ S_3 \end{bmatrix}_{out} = \begin{bmatrix} M_{11} & M_{12} & M_{13} & M_{14} \\ M_{21} & M_{22} & M_{23} & M_{24} \\ M_{31} & M_{32} & M_{33} & M_{34} \\ M_{41} & M_{42} & M_{43} & M_{44} \end{bmatrix} \begin{bmatrix} S_0 \\ S_1 \\ S_2 \\ S_3 \end{bmatrix}_{in} \quad (1)$$

In a spectral polarimetric detector, it is desirable to measure the Mueller matrix for each distinct wavelength band of the system. Thus, the measurement and calculation of the Mueller matrix are desirably repeated over each wavelength range used. This process is described in further detail below with reference to FIG. 7

The Mueller matrix is used to calculate the Stokes images from a collected spectral polarimetric images. The Mueller matrix is essentially a calibration matrix for the polarization effects of the imager. In an ideal system, the matrix would has values of 1 along the diagonal axis as follows:

$$\begin{bmatrix} 1000 \\ 0100 \\ 0010 \\ 0001 \end{bmatrix} \quad (2)$$

This indicates that each of the polarizers is perfect and does not let any light pass which does not match the polarization state of the polarizer. In practice this may not be the case and there may be some values that are not along the diagonal axis that are non-zero. This is partially due to the filters not being perfect and the optics before the polarizers changing the polarization state of the calibrated light sources (e.g., most optics will slightly depolarize light passing thru them). The advantage of using the Mueller matrix to calculate the Stokes images is that the Mueller matrix corrects for imperfections within the system and provides a calibrated Stokes image. If it is determined that the spectral polarimetric system is near ideal, the step of block 602 may be omitted.

At block 604, spectral polarimetric images are obtained. In an exemplary embodiment, the spectral polarimetric images are intensity images of each polarization state, e.g., $I_0, I_1, I_2, I_3$, in each spectrally selected wavelength band, e.g., $\lambda_0\text{-}\lambda_6$, obtained using the spectral polarimetric detector 100.

At block 606, the spectral polarimetric images are converted to Stokes images. The intensity images of each polarization state of the spectral polarimetric images may be converted to Stokes images using equations 3-6.

$$S_0 = 2I_0 \quad (3)$$

$$S_1 = 2I_1 - 2I_0 \quad (4)$$

$$S_2 = 2I_2 - 2I_0 \quad (5)$$

$$S_3 = 2I_3 - 2I_0 \quad (6)$$

At block 608, the Stokes images are calibrated using the calibration matrices generated at block 602. If the spectral polarimetric detector 106 is near ideal, the calibration of step 608 may be omitted. Additional information describing the conversion of spectral polarimetric images to Stokes images of step 606 and the calibration of the Stokes images in step 608 are described in further detail below with reference to FIG. 8

At block 610, the Stokes images are saved, e.g., in memory 130 by processor 128. Is will be recognized by one skilled in the art that the Stokes images may be saved before calibration with the Stokes images being calibrated at a later time. Thus, the step of block 610 may be performed prior to the step of block 608.

At block 612, two or more of the Stokes images are selected for display. In an exemplary embodiment, three of the Stokes images are selected for presentation on a display 132. The use of three Stokes images may be selected since, in general, humans are used to seeing only three combinations of colors at a time (Red, Green, Blue) on a monitor. Thus, three bands may be selected from the multiple bands to display (e.g., as Red, Green, Blue combinations on a display 132 of a monitor). For example, for four (4) Stokes images for each of the 26 wavelength bands (e.g., $A_{S0}, A_{S1}, A_{S2}, A_{S3}, B_{S0}, B_{S1}, B_{S2}, B_{S3}, \ldots Z_{S0}, Z_{S1}, Z_{S2}, Z_{S3}$), any of these bands may be selected for display in the Red, Green and Blue channels of a monitor ($D_{S0}$=Red, $K_{S0}$=Blue and $Q_{S0}$=Green or $D_{S0}$=Red, $D_{S1}$=Blue and $D_{S2}$=Green, etc.). The selection of the exact band and polarization combinations can be performed by an algorithm that finds anomalies or by a priori knowledge of the object/target/signature of interest.

Figure 7:
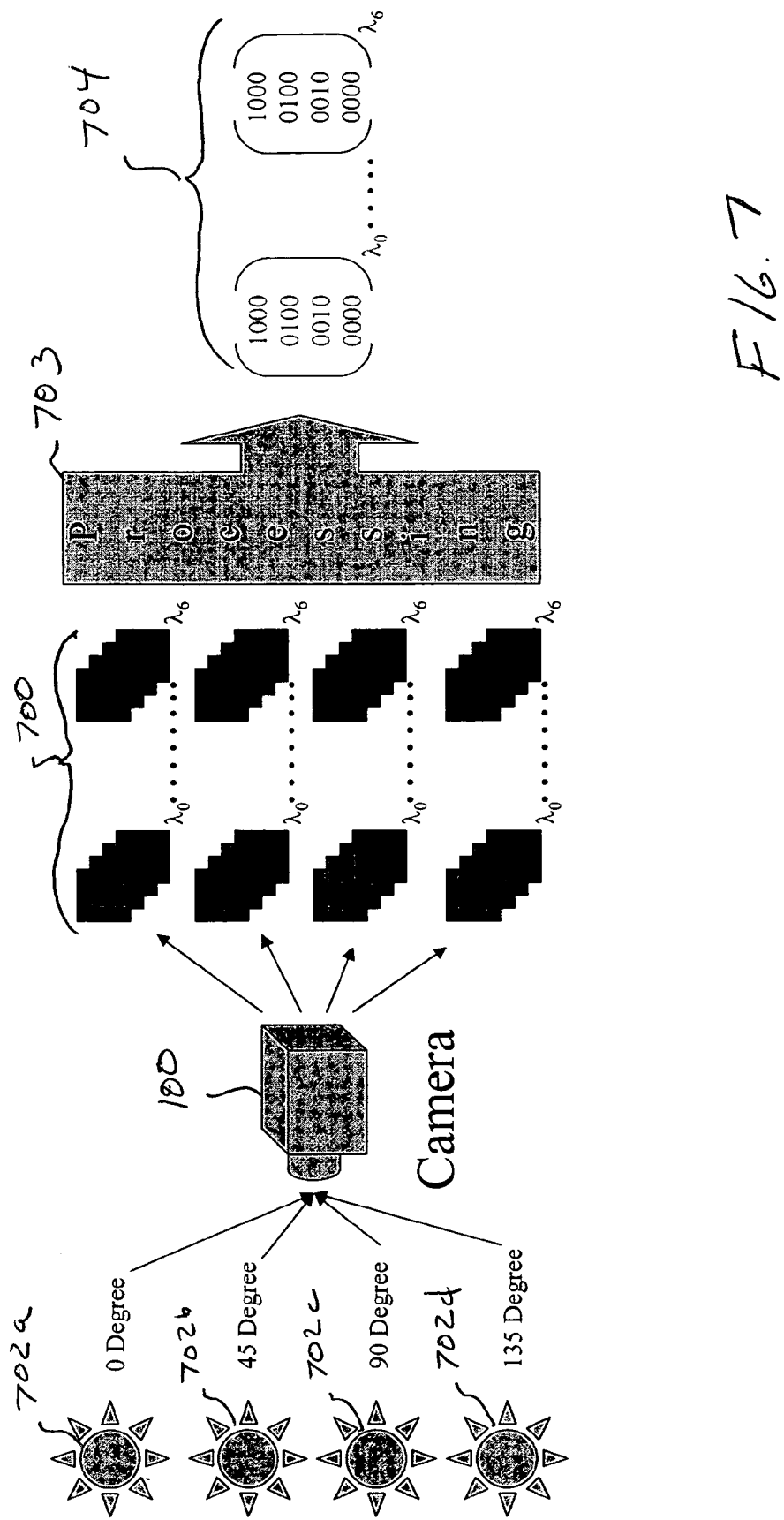
FIG. 7 is a conceptual illustration of a calibration procedure for spectral polarimetric images in accordance with aspects of the present invention.

FIG. 7 illustrates a calibration procedure for generating Mueller matrices. In FIG. 7, a spectral polarimetric detector 100 captures spectral polarimetric images of four polarized calibration images 702*a-d*. In an exemplary embodiment, the polarized calibration images 702 includes a 0° polarized calibration image 702*a*, a 45° polarized calibration image 702*b*, a 90° polarized calibration image 702*c*, and a 135° polarized calibration image 702*d* that are sequentially imaged by the spectral polarimetric detector 100 in seven wavelength ranges $\lambda_0\text{-}\lambda_6$. The spectral polarimetric images, in this case 112 images, are then processed by a processor 703 in a manner that will be understood by one of skill in the art from the description herein to generate the Mueller matrices 704 for each wavelength range. Ideally, the diagonal elements within the Mueller matrix 704 correspond to one of the polarimetric states, e.g., 0°, 45°, 90°, and 135°. Ideally, the element corresponding to a particular state, e.g., 0°, has a normalized value of one when the 0° polarized calibration image 702*a* is captured and a value of zero when other polarized calibration images 702*b-d* are captured.

FIG. 8 illustrates the generation of Stokes images in accordance with an exemplary embodiment of the present invention. In FIG. 8, a spectral polarimetric detector 100 captures spectral polarimetric images 800 of a target 802. In an exemplary embodiment, the spectral polarimetric images include an intensity image for each polarimetric state for each wavelength band of interest. The spectral polarimetric images are then processed using the Muller matrix 704 (FIG. 7) in a manner that will be understood by one of skill in the art from the description herein to generate Stokes images for each wavelength of interest (e.g., S0, S1, S2, etc.).

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A spectral polarimetric detection apparatus for detecting light received from a light source, the apparatus comprising:
    a tunable spectral selector that selects one or more spectral bands of light within the received light; and
    a polarimetric imager optically coupled to the tunable spectral selector to receive the selected one or more spectral bands of light, the polarimetric imager configured to capture the selected one or more spectral bands of light.

2. The apparatus of claim 1, wherein the tunable spectral selector includes:
    a grating that disperses the received light; and
    a spectral selection device that selects the one or more spectral bands of light from within the dispersed light.

3. The apparatus of claim 2, wherein the spectral selection device is a Grating Electro-Mechanical System (GEMS) device.

4. The apparatus of claim 2, wherein the spectral selection device is a Liquid Crystal on Silicon (LCOS) light modulator.

5. The apparatus of claim 2, wherein the spectral selection device is digital micromirror device.

6. The apparatus of claim 2, wherein the spectral selection device selectively diffracts the one or more spectral bands within the dispersed light back toward the light path selector to select the one or more spectral bands of light and wherein the grating collimates the diffracted dispersed light.

7. The apparatus of claim 6, wherein the light is received along an optical path and wherein the apparatus further comprises:
    a light path selector positioned along the optical path, the light path selector passing light from the light source through to the spectral selection device and reflecting the selected one or more spectral bands of light selectively diffracted by the spectral selection device toward the polarimetric imager.

8. The apparatus of claim 7, wherein the light path selector is a patterned mirror.

9. The apparatus of claim 7, wherein the light path selector is a dichroic element.

10. The apparatus of claim 7, further comprising:
    an input lens assembly configured to direct the received light toward the tunable spectral selector, wherein the light path selector and the transmission grating are positioned within a Fourier transform plane of the input lens assembly.

11. The apparatus of claim 1, wherein the tunable spectral selector selects the one or more spectral bands of light responsive to a spectral selection signal and wherein the apparatus further comprises:
    a processor coupled to the tunable spectral selector, the processor configured to generate the spectral selection signal.

12. The apparatus of claim 1, wherein the processor is further coupled to the polarimetric imager, the processor configured to obtain data from the polarimetric imager.

13. A spectral polarimetric detection apparatus for detecting light received from a light source along an optical path, the apparatus comprising:
    a spectral selection device adapted to select one or more spectral bands of light from a dispersion of the received light by selectively diffracting the dispersion of the received light responsive to a spectral selection signal;
    a grating that disperses the received light toward the spectral selection device for selection of the one or more spectral bands of light by the spectral selection device and that collimates the selectively diffracted dispersion of the received light;
    a polarimetric imager that captures the selected one or more spectral bands of light to develop image data;
    a light path selector positioned along the optical path, the light path selector passing light from the light source toward the grating for dispersion and reflecting the collimated selected one or more spectral bands received from the grating toward the polarimetric imager; and
    a processor coupled to the spectral selection device and the polarimetric imager, the processor generating the spectral selection signal and processing the image data.

14. The apparatus of claim 13, wherein the spectral selection device is a Grating Electro-Mechanical System (GEMS) device.

15. The apparatus of claim 13, wherein the light path selector is a patterned mirror having an opening and wherein the apparatus further comprises:
    a first lens assembly configured to direct the received light through the opening in the patterned mirror toward the transmission grating for dispersion;
    a second lens assembly configured to focus the dispersed light on the spectral selection device; and
    a third lens assembly configured to focus the reflected collimated selected one or more spectral bands on the polarimetric imaging device.

16. A spectral polarimetric detection method for detecting light received from a light source, the method comprising the steps of:
    directing light to a tunable spectral selection device;
    selecting one or more spectral bands by the spectral selection device;
    sending the one or more spectral bands, selected by the spectral selection device, to a polarimetric imager; and
    capturing, by the polarimetric imager, at least one polarimetric image of the selected one or more spectral bands of light.

17. The method of claim 16, wherein the capturing step comprises the step of:
    capturing the at least one polarimetric image in two or more polarimetric states.

18. The method of claim 16, wherein the capturing step comprises the step of:
    capturing the at least one polarimetric image in four polarimetric states.

19. The method of claim 16, wherein the selecting step comprises the steps of:
    dispersing the received light;
    selectively diffracting the dispersed light to select the one or more spectral bands of light; and
    collimating the selectively diffracted one or more spectral bands of light for capturing of the at least one polarimetric image.

20. The method of claim 19, further comprising the steps of:
    passing the received light through a patterned mirror prior to selecting the one or more spectral bands of light; and
    reflecting the selectively diffracted one or more spectral bands of light with the patterned mirror prior to capturing the at least one polarimetric image.

* * * * *